(12) United States Patent
Isozaki et al.

(10) Patent No.: US 6,941,792 B2
(45) Date of Patent: Sep. 13, 2005

(54) SURFACE INSPECTION SYSTEM

(75) Inventors: Hisashi Isozaki, Tokyo-to (JP); Masanori Matsuda, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 10/213,607

(22) Filed: Aug. 6, 2002

(65) Prior Publication Data
US 2003/0029220 A1 Feb. 13, 2003

(30) Foreign Application Priority Data

Aug. 10, 2001 (JP) ........................................ 2001-243939
Jun. 21, 2002 (JP) ........................................ 2002-181136

(51) Int. Cl.⁷ .............................................. G01B 11/00
(52) U.S. Cl. .................... 73/1.79; 73/865.8; 356/243.4; 356/243.7; 702/104
(58) Field of Search ............................. 73/865.8, 1.01, 73/1.79; 356/243.4, 243.6, 243.7; 250/559.4; 702/104, 105

(56) References Cited

U.S. PATENT DOCUMENTS

| | | | | |
|---|---|---|---|---|
| 5,472,086 A | * | 12/1995 | Holliday et al. | ............ 206/711 |
| 5,550,634 A | * | 8/1996 | Nakamura | .................. 356/401 |
| 5,691,812 A | * | 11/1997 | Bates et al. | ............. 356/243.4 |
| 2001/0048523 A1 | * | 12/2001 | Fossey et al. | ............. 356/237.2 |

FOREIGN PATENT DOCUMENTS

| | | | | |
|---|---|---|---|---|
| JP | 62118535 A | * | 5/1987 | ........... H01L/21/68 |
| JP | 066730 A1 | * | 3/1994 | ........... G01N/21/88 |
| JP | 338440 A1 | * | 12/1994 | ........... H01L/21/02 |
| JP | 2001118895 A | * | 4/2001 | ........... H01L/21/66 |

* cited by examiner

Primary Examiner—Hezron Williams
Assistant Examiner—Nashmiya Fayyaz
(74) Attorney, Agent, or Firm—Nields & Lemack

(57) ABSTRACT

A surface inspection system, comprising a calibration wafer where particles of known specifications are spread, a wafer transport unit having a transport robot, a surface inspection unit, and a calibration wafer accommodation unit for accommodating the calibration wafer.

9 Claims, 6 Drawing Sheets

SURFACE INSPECTION SYSTEM

BACKGROUND OF THE INVENTION

The present invention relates to a surface inspection system used in inspection process in manufacture of a semiconductor and for inspecting whether foreign objects such as particles spread on a wafer surface are present or not.

A surface inspection system for a wafer is designed so that a laser beam is projected to a surface of the wafer under high-speed rotation, and the laser beam scans the entire surface of the wafer while a laser beam projecting position is moved at a predetermined pitch or at a predetermined rate in a radial direction, and a light reflected from the surface of the wafer is detected. The reflected light is scattered by foreign objects on the surface of the wafer. The scattering condition differs according to the particle size of the foreign object. From the change in the conditions of the detected scattered light, it is possible to identify whether there is foreign object or not and the size of foreign object.

Sensitivity and Responsiveness of a photodetection sensor, which detects the scattered light, can be adjusted by voltage applied on the photodetection sensor. That is, by maintaining the voltage applied on the photodetection sensor at an adequate level, it is possible to detect foreign objects in stable manner. For this reason, when the surface inspection of the wafer is performed, the responsiveness of the photodetection sensor is adjusted (calibrated) by using a calibration wafer, which has the same characteristics as the wafer to be inspected and which is coated with standard particles with a predetermined diameter and in a predetermined number of particles.

In the past, the calibration of the photodetection sensor has been performed as follows: Prior to starting of the inspection, a calibration wafer is brought into the surface inspection system from outside of the surface inspection system at each inspection, and the calibration wafer is loaded on a wafer chuck in the surface inspection system.

A laser beam is projected to the calibration wafer, and the scattered light is received by the photodetection sensor. Then, the voltage applied on the photodetection sensor is adjusted in such manner that spreading condition of foreign objects detectable under photodetecting condition matches with data already known of the calibration wafer.

In the conventional type surface inspection system described above, the calibration wafer is brought in or out manually by an operator, and this results in low working efficiency. Also, the calibration wafer acts as a reference, and it must not be contaminated with particles spread on it. However, because the manual work is involved, there is high possibility that particles are spread on the wafer surface. Because the calibration wafer is brought in from outside or brought out to outside, the surface inspection of the wafer cannot be carried out immediately after the adjustment of sensitivity of the photodetection sensor, and it is unavoidable that a certain time elapses before the surface inspection is performed. For this reason, the changes over time such as drift may occur on the responsiveness of the photodetection sensor, and this may exert influence on detection error.

Further, the calibration wafer must be kept under clean atmosphere outside the surface inspection system. This means that an additional storage space for the calibration wafer or an equipment similar to such storage system is required.

SUMMARY OF THE INVENTION

It is an object of the present invention to provide a surface inspection system, by which it is possible to improve inspection efficiency without involvement of manual operation in calibration process of the surface inspection system, to avoid contamination of a calibration wafer with particles, etc., and further to prevent changes over time of responsiveness of a photodetection sensor so as to improve detection accuracy.

To attain the above object, the surface inspection system according to the present invention comprises a calibration wafer where particles of known specifications are spread, a wafer transport unit having a transport robot, a surface inspection unit, and a calibration wafer accommodation unit for accommodating the calibration wafer. Also, the present invention provides a surface inspection system as described above, the calibration wafer accommodation unit is designed as an airtight dustproof space, which can be opened and closed. Further, the present invention provides a surface inspection system as described above, the calibration wafer accommodation unit is provided in the wafer transport unit. Also, the present invention provides a surface inspection system as described above, the calibration wafer accommodation unit is provided in the surface inspection unit. Further, the present invention provides a surface inspection system as described above, the calibration wafer accommodation unit holds and accommodates the calibration wafer in a vertical position. Also, the present invention provides a surface inspection system as described above, the calibration wafer accommodation unit is arranged at a position above a wafer receiving plane of the surface inspection unit. Further, the present invention provides a surface inspection system as described above, a clean unit is provided in the wafer transport unit, the clean unit delivers clean air into the wafer transport unit, and the calibration wafer accommodation unit is positioned upstream of a flow of the clean air with respect to the transport robot. Also, the present invention provides a surface inspection system as described above, the surface inspection unit comprises a computer, which has a wafer surface inspection program, a calibration program, and a transport robot driving program, wherein the transport robot driving program, the surface inspection program, and the calibration program are executed, and bringing of the calibration wafer into the surface inspection unit by the transport robot, surface inspection of the calibration wafer, execution of calibration, and bringing out of the calibration wafer are sequentially carried out. Further, the present invention provides a surface inspection system as described above, an inert gas atmosphere is used as the atmosphere where the calibration wafer is accommodated. Also, the present invention provides a surface inspection system as described above, an inert gas is filled in the calibration wafer accommodation unit. Further, the present invention provides a surface inspection system as described above, the surface inspection unit comprises a computer, the calibration wafer accommodation unit accommodates two or more calibration wafers and the computer records a transport history of each of the calibration wafers.

DETAILED DESCRIPTION OF THE PREFERRED EMBODIMENTS

Figure 1:
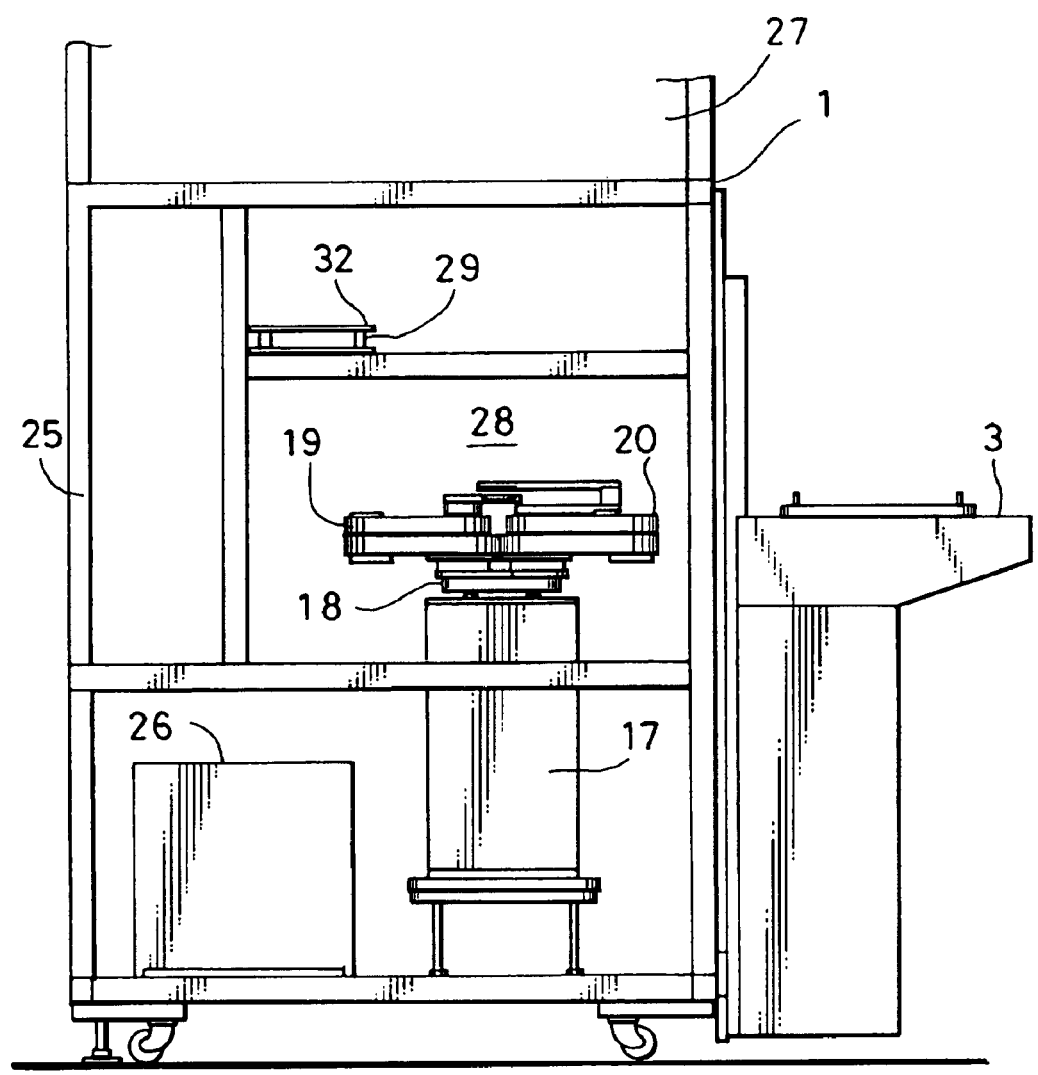
FIG. 1 is a side view showing an essential portion of an embodiment of the present invention.
Figure 2:
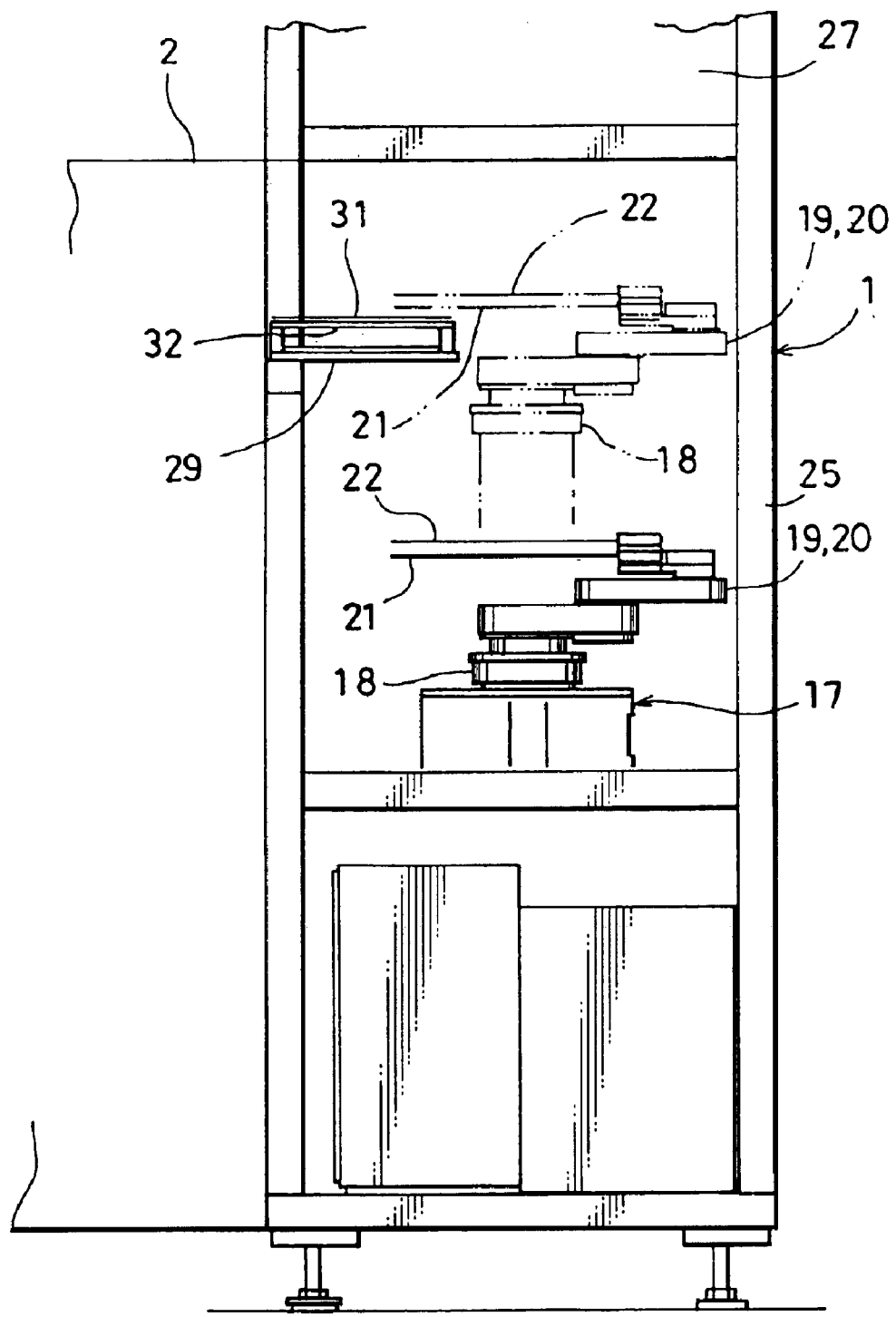
FIG. 2 is a rear view showing an essential portion of the embodiment of the present invention.

Description will be given below on embodiments of the present invention referring to the drawings.

First, referring to FIG. 1 to FIG. 6, description will be given on a surface inspection system according to the present embodiment.

The surface inspection system is installed in a clean room.

Figure 3:
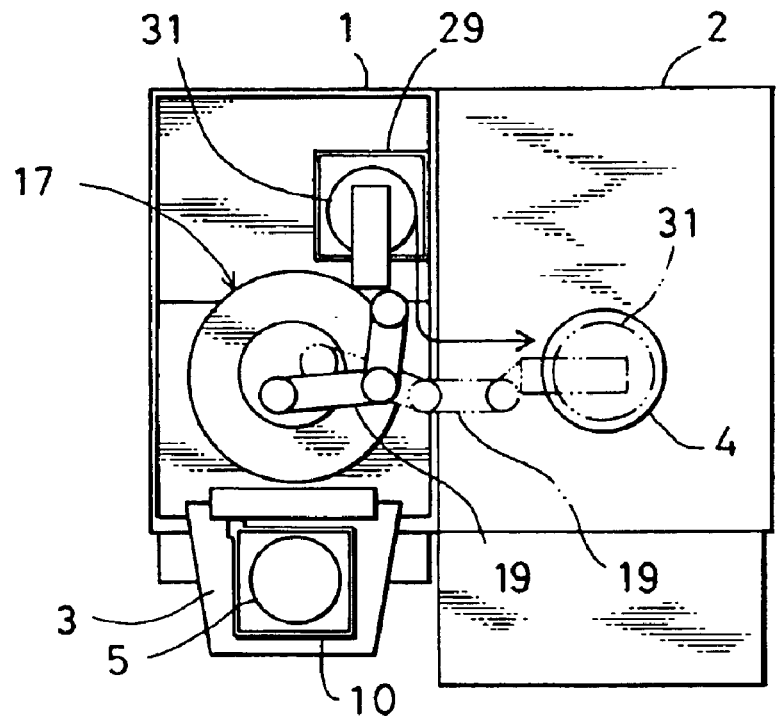
FIG. 3 is a plan view showing the embodiment of the present invention.

As shown in FIG. 3, a surface inspection unit 2 is positioned adjacent to one side of a wafer transport unit 1, and a cassette transfer stage 3 is positioned adjacent to another side of the wafer transport unit 1.

Figure 6:
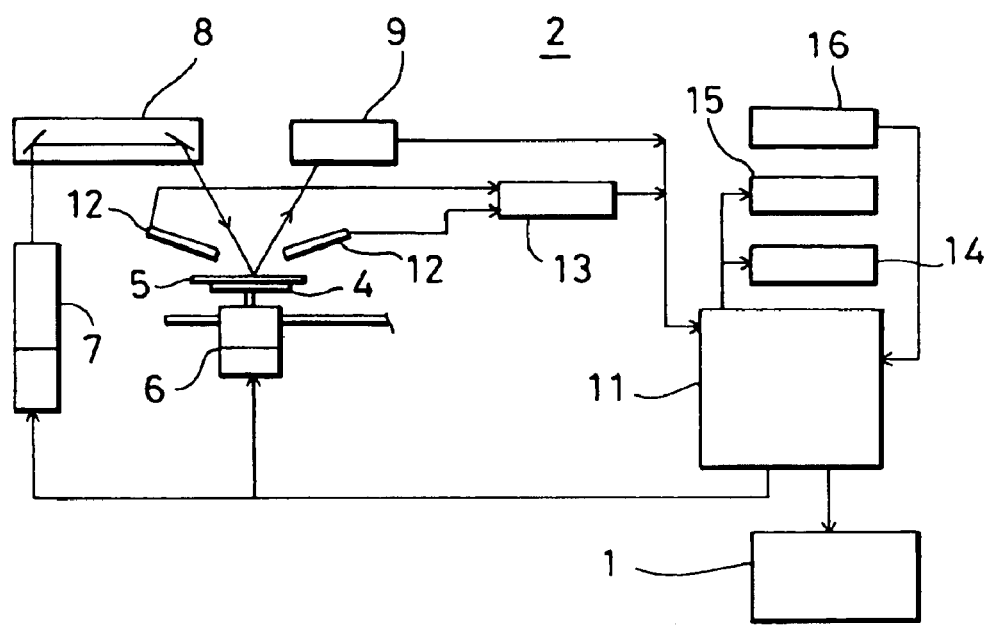
FIG. 6 is a system block diagram of the embodiment of the present invention.

As shown in FIG. 6, the surface inspection unit 2 comprises an inspection table 4, on which a wafer 5 is to be placed, a motor 6 for rotating the inspection table 4 at high speed, a laser light source for emitting a laser beam for inspection, a light projector 8 for projecting the laser beam toward a surface of the wafer 5, a photodetection unit 9 for receiving a reflected light of the laser beam from the surface of the wafer 5 and for converting the photodetection status to an electric signal and then inputting the electric signal to a computer 11, a photodetection sensor 12 for detecting scattered light reflected by the surface of the wafer 5, and a signal processing unit 13 for amplifying a photodetection signal from the photodetection sensor 12 and outputting the signal to the computer 11 after required signal processing such as A/D conversion. Based on the signal from the photodetection unit 9, the computer 11 controls light emitting condition of the laser light source 7 and the computer 11 calculates values such as number of particles spread on the wafer 5 based on the signal from the signal processing unit 13.

The result of calculation by the computer 11, i.e. the result of surface inspection, is outputted to a printer 14 and a monitor 15. Also, an inspection starting command or an inspection condition, etc. is inputted from an operation unit 16.

A surface inspection program is incorporated in the computer 11. Also, a sequence program for driving and controlling a transport robot 17 of the wafer transport unit 1 is incorporated in the computer 11. The computer 11 issues a control signal to bring the wafer 5 in and out of the wafer transport unit 1. As to be described later, a program for performing surface inspection of the wafer to be inspected and a calibration program are included in the surface inspection program. The calibration program can be automatically operated according to the predetermined conditions. These conditions are: timing to change the wafer 5 to be inspected, duration of the surface inspection, number of inspections, time to use the laser light source 7, the level of contamination within the system, etc. The inspection program can also be operated according to an intention of an operator instead of automatic operation.

A cassette 10 loaded with the wafer 5 is transported to the cassette transfer stage 3 and is placed on it.

The wafer transport unit 1 primarily comprises a frame 25, a closed housing containing a panel (not shown) mounted on the frame 25, a power source (not shown) installed on a lower portion of the housing, a drive unit 26, the transport robot 17 erected on a bottom surface of the housing, and a clean unit 27 installed on an upper portion of the housing, etc. These components make up together a wafer transport space 28 in a middle portion of the housing.

The clean unit 27 delivers purified air in a downward direction so that a stream of clean air flowing downward from above is formed in the wafer transport space 28.

The transport robot 17 comprises a lift 18, and two sets of arms 19 and 20 provided on an upper end of the lift 18. Wafer receiving plates 21 and 22 are arranged on a forward end of each of the arms 19 and 20 respectively.

The arms 19 and 20 are designed in a complex arm structure. When the arms 19 and 20 are extended or contracted, the wafer receiving plates 21 and 22 are independently moved back and forth, and the arms 19 and 20 are also rotatable.

A calibration wafer accommodation unit 29 is mounted on the frame 25 within an operating range of the transport robot 17 so that the calibration wafer accommodation unit 29 is positioned above the wafer transport space 28. The calibration wafer accommodation unit 29 is arranged in the stream of clean air as described above. The desirable arrangement is such that there is no obstacle upstream of the calibration wafer accommodation unit 29 and the stream of clean air evenly flows around the calibration wafer accommodation unit 29 and there is no stagnation of the air.

Dust is generated by transport operation of the transport robot 17. Because the calibration wafer accommodation unit 29 is positioned above the transport robot 17, the calibration wafer accommodation unit 29 is positioned upstream of the stream of the clean air. As a result, particles generated by the transport robot 17 do not reach the calibration wafer accommodation unit 29.

The calibration wafer accommodation unit 29 has two wafer receiving plates 32 in upper and lower stages where a calibration wafer 31 is to be placed. The calibration wafer 31 held by the calibration wafer accommodation unit 29 has a plurality of partitioned areas. On each of these areas, particles of predetermined material (PSL) are spread and particle size, number of particles or distribution density are different depending on each area. Thus, a plurality of calibration conditions can be obtained by the single calibration wafer 31.

As described above, the stream of clean air with no stagnation is formed around the calibration wafer accommodation unit 29, i.e. around the calibration wafer 31 accommodated in it. Thus, particles contained in slight quantity in the clean air are not attached to the calibration wafer 31, and a surface of the calibration wafer 31 is always maintained in clean condition.

It may be designed in such manner that the calibration wafer 31 can be held and accommodated in a vertical position in the calibration wafer accommodation unit 29. When the calibration wafer 31 is held in a vertical position, the calibration wafer 31 is set in parallel to the stream of the clean air, and this makes the attachment of the particles much more difficult.

When the calibration wafer 31 is accommodated in a vertical position in the calibration wafer accommodation unit 29, the transport robot 17 is provided with a function to rotate a position of the wafer at an angle of 90°. Or, the calibration wafer accommodation unit 29 itself may be rotated after the calibration wafer 31 is accommodated. The means for rotating the calibration wafer 31 can be adequately selected so that the calibration wafer 31 is held in a vertical position when the calibration wafer 31 is accommodated in the calibration wafer accommodation unit 29.

Further, with the purpose of preventing attachment of dust on the calibration wafer 31 accommodated in the calibration wafer accommodation unit 29, the calibration wafer accommodation unit 29 may be designed as a closed container with a transport port, which can be opened or closed when desired.

Also, the calibration wafer accommodation unit 29 may be designed merely as a shelf, and the cassette 10 for wafer transport may be installed in the calibration wafer accommodation unit 29 instead of designing as a closed container.

In the following, description will be given on transport operation of the wafer.

Figure 5:
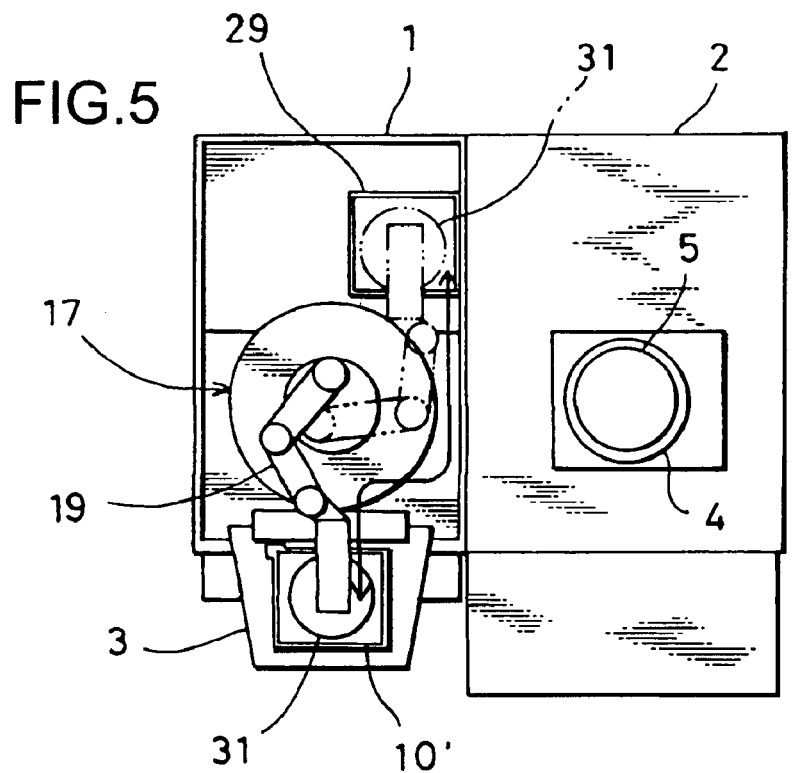
FIG. 5 is a plan view showing the embodiment of the present invention.

First, description will be given on transport of the calibration wafer 31 referring to FIG. 5.

A cassette 10' accommodating the calibration wafer 31 in it is transported to the cassette transfer stage 3. In the cassette 10', one calibration wafer 31 or two or more calibration wafers 31 are accommodated. When two or more wafer calibration wafers 31 are accommodated, the calibration wafers 31 are selected in such manner that these wafers are different from each other in particle size, number of particles attached on the wafers, or particle distribution density.

The transport robot 17 is moved up or down to a transport level of the calibration wafer 31. By cooperative movement of rotation, extension and contraction of whichever of the arms 19 or 20 (description will be given below only on the arm 19), the calibration wafer 31 in the cassette 10' is held. By cooperative movement of moving up or down of the lift 18 and extension, contraction and rotation of the arm 19, the calibration wafer 31 is delivered from the cassette 10'. Then, the calibration wafer 31 is taken into the wafer transport unit 1. With the rotation of the arm 19, the lift 18 is moved up. When the transport level is aligned with the height of the calibration wafer accommodation unit 29, the calibration wafer 31 is moved to the calibration wafer accommodation unit 29 by cooperative movement of rotation, extension and contraction of the arm 19 and the moving up or down of the lift 18.

In case there are two or more calibration wafers 31, transport history, etc. of each calibration wafer 31 is stored in the computer 11, and the type of the calibration wafer 31 is correlated with accommodating position of the wafer in the calibration wafer accommodation unit 29.

The transport operation as described above is repeated, and all of the calibration wafers 31 are transported from the cassette 10' to the calibration wafer accommodation unit 29.

The cassette 10' is removed, and the cassette 10 accommodating the wafer 5 to be inspected is transported to the cassette transfer stage 3.

In the preliminary process prior to the surface inspection of the wafer 5, the detection unit (the photodetection sensor 12 and the signal processing unit 13) is calibrated.

First, as shown in FIG. 3, the calibration wafer 31 is transported to the inspection table 4. In case there are two or more calibration wafers 31 accommodated in the calibration wafer accommodation unit 29, a calibration wafer 31 to be transported is selected, which corresponds to the wafer 5. For instance, a wafer having the same film quality or a wafer having the conditions (particle size, number of particles, or particle distribution density) which match those of the wafer 5 is selected.

The transport robot 17 is moved up, and the calibration wafer 31 in the calibration wafer accommodation unit 29 is held by cooperative movement of rotation, extension and contraction of whichever of the arm 19 or 20 (description will be given below only on the arm 19). By cooperative movement of extension, contraction and rotation of the arm 19, the calibration wafer 31 is delivered from the calibration wafer accommodation unit 29, and the transport robot 17 is moved down further. Then, the calibration wafer 31 is placed on the inspection table 4 in the surface inspection unit 2 by rotation of the transport robot 17 and by extension and contraction of the arm 19.

The arm 19 is retracted from the surface inspection unit 2, and the surface inspection is carried out on the calibration wafer 31.

The inspection table 4 is rotated by the motor 6, and a laser beam is projected onto the calibration wafer 31 via the light projector 8. The light reflected by the calibration wafer 31 is received by the photodetection unit 9, and the result of photodetection is inputted to the computer 11. Based on the photodetection result, the computer 11 controls the laser light source 7 so that the projection of the laser beam to the calibration wafer 31 is maintained in constant condition.

If there are foreign objects such as particles on the surface of the calibration wafer 31, the laser beam is turned to scattered light. This scattered light is detected by the photodetection sensor 12. The conditions of the scattered light correspond to particle size and number of the foreign objects.

On the calibration wafer 31, foreign objects are spread under the conditions already known (particle size of foreign object, number of particles, or distribution density, etc. are already known). Thus, calibration is carried out by checking and matching the photodetection signal obtained from the photodetection sensor 12 with the data already known on the surface condition of the calibration wafer 31. For calibration, a voltage applied on the photodetection sensor 12 is adjusted and sensitivity of the photodetection sensor 12 is adjusted. Or, amplification ratio of the photodetection signal at the signal processing unit 13 is adjusted. Or, calibration is carried out by adequate methods such as both of these two methods are carried out.

When calibration is completed, the calibration wafer 31 on the inspection table 4 is moved out by the transport robot 17 and the calibration wafer 31 is brought back to the calibration wafer accommodation unit 29 by the arm 19.

Figure 4:
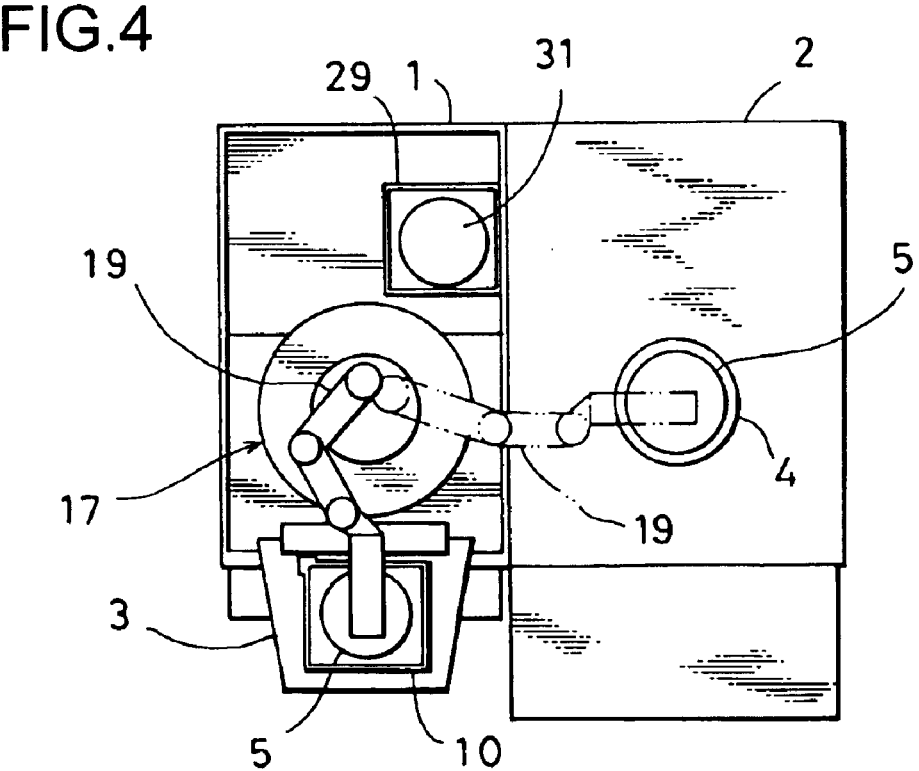
FIG. 4 is a plan view showing the embodiment of the present invention.

Next, as shown in FIG. 4, the wafer 5 to be inspected is taken from the cassette 10 on the cassette transfer stage 3 and is transported to the inspection table 4.

By cooperative movement of moving up or down, rotation, extension and contraction, the transport robot 17 delivers the wafer 5 from the cassette 10 and transports the wafer 5 to the inspection table 4. Then, the arm 19 is retracted from the surface inspection unit 2.

The laser beam is projected to the wafer 5 from the light projector 8, and the scattered light is detected by the photodetection sensor 12. The scattered light is converted to an electric signal by the photodetection sensor 12, and the signal is processed by the signal processing unit 13 and is inputted to the computer 11. Based on the signal from the signal processing unit 13, the computer 11 calculates number of foreign objects, particle size of the foreign object, etc. The result of the calculation is stored in storage means such as hard disk (not shown) and is further displayed on the monitor 15.

When the surface inspection of the first wafer 5 has been completed, the first wafer 5 is brought back to the cassette 10 from the inspection table 4 by the transport robot 17, and the surface inspection of a second wafer 5 is carried out.

Reflectivity and reflecting condition on the surface of the wafer 5 differs respectively according to the type of film formed on the surface of the wafer 5. When the type of film on the wafer 5 to be inspected is changed, calibration is performed also on change of the film type.

By giving consideration on the change of film type, the calibration wafers 31 are accommodated in the calibration wafer accommodation unit 29 so that two or more calibration wafers 31 of different film types are accommodated in it. Then, the calibration wafers 31 are selected according to each film type of the wafer 5 so that optimal calibration can be carried out.

Also, the calibration wafer accommodation units 29 may be provided at two or more positions. For instance, in FIG. 3, the calibration wafer accommodation units 29 may be provided symmetrically at two positions, and it is possible to increase the number of the calibration wafers 31 to be accommodated.

Figure 7:
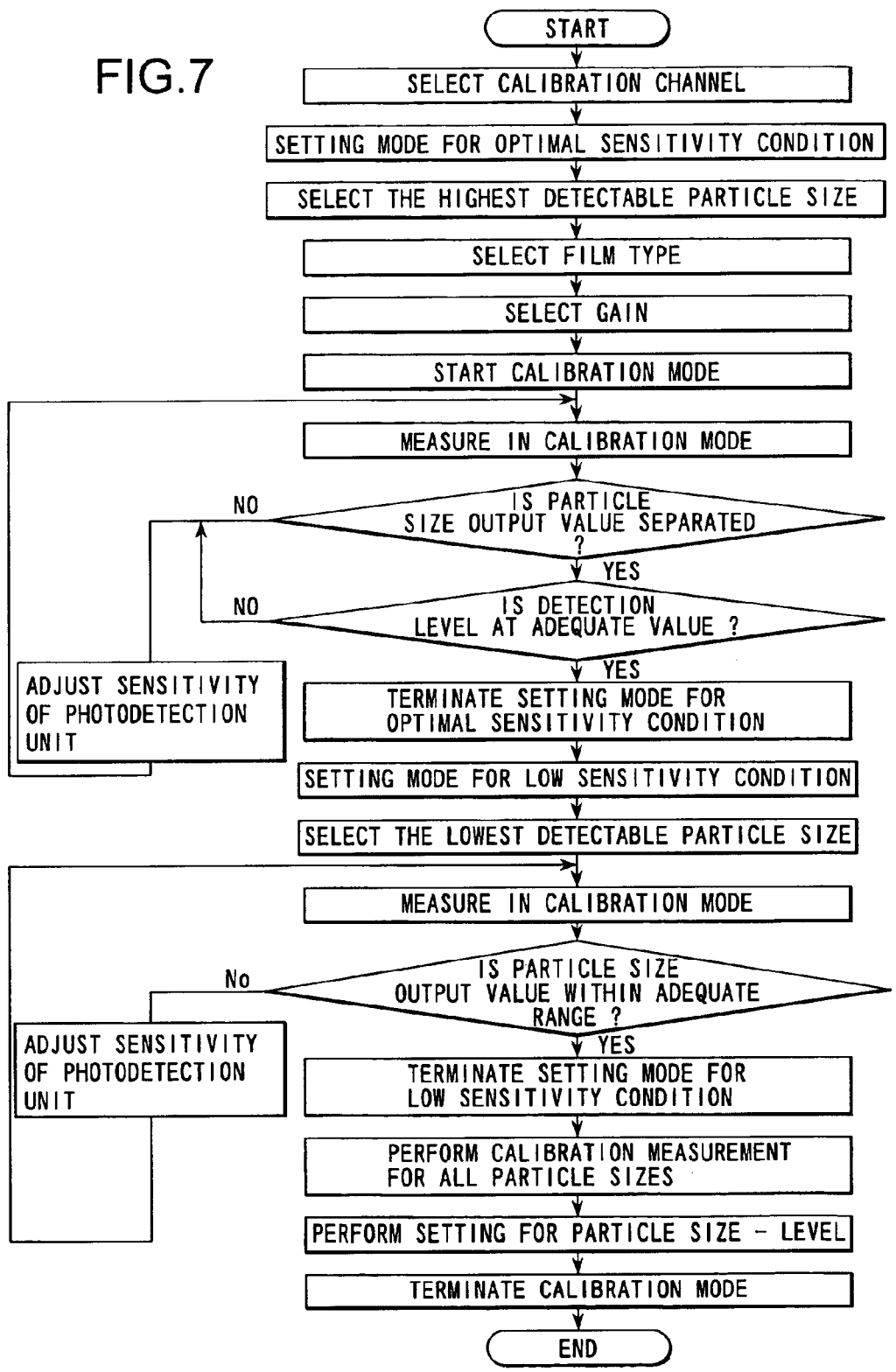
FIG. 7 is a flow chart showing calibrating operation of the embodiment of the present invention.

Referring to FIG. 7, detailed description will be given on calibrating operation.

The sequence operation to transport the calibration wafers 31 from the cassette 10' to the calibration wafer accommodation unit 29 is stored in the computer 11 as a program to transport the calibration wafer. The operator can directly start the calibration wafer transport program from the operation unit 16 of the surface inspection system so as to transport the calibration wafer 31. Or, as to be described later, it can be incorporated in the surface inspection program, and the transport of the calibration wafer 31 can be carried out as one of the processes of the surface inspection.

From the operation unit 16, a START command is given.

The surface inspection program is started, and an inspection menu picture is displayed on the monitor 15.

Based on the inspection menu picture, the transport of the calibration wafer 31 is selected, and the transport menu picture is started. Then, the operator teaches the computer 11 via the operation unit 16 as to which specifications of the calibration wafers 31 (i.e. film quality, particle size, number of particles, or distribution density) is accommodated in the cassette 10'. In particular, in case there are two or more calibration wafers 31, the operator teaches the computer via the operation unit 16 at which position of the cassette 10' the calibration wafer 31 is accommodated and which specifications of the calibration wafer 31 is loaded.

The instruction is given to start the transport, and the calibration wafer 31 is transported from the cassette 10' of the cassette transfer stage 3 to the calibration wafer accommodation unit 29.

Transport history of the calibration wafer 31 is stored in the computer 11, and the computer 11 stores at which position of the calibration wafer accommodation unit 29 the calibration wafer 31 has been accommodated, and which specifications of the calibration wafer 31 is accommodated.

The inspection menu picture is started, and the inspection is started.

From the inspection menu picture, a calibration channel is selected. Further, as the calibration channel, inspecting conditions (such as selection of a scanning pitch in a radial direction) are selected. When surface inspection is performed on a wafer to be inspected, execution of the inspection is selected on this inspection menu picture.

A setting mode for optimal sensitivity condition is further selected on the inspection menu picture. Further, the highest detectable particle size is selected, and the inspecting condition is set to have the optimal sensitivity.

The type of the film on the surface of the wafer to be inspected is selected. In order to set sensitivity characteristics of the system, gain is selected.

When the above inspection conditions have been inputted, the computer 11 judges whether the calibration wafer 31 which matches the inputted conditions is accommodated in the calibration wafer accommodation unit 29 or not. If it is not accommodated, the inspection is stopped, and the fact that the corresponding calibration wafer 31 is not accommodated is displayed on the monitor 15. Or, the required specifications of the calibration wafer 31 is displayed, and the operator is instructed to replace or replenish the calibration wafer 31. When a cassette 10' accommodating an adequate calibration wafer 31 is placed on the cassette transfer stage 3, the calibration wafer 31 accommodated in the calibration wafer accommodation unit 29 is replaced with the adequate calibration wafer 31.

In case a calibration wafer 31 corresponding to the surface inspecting condition is accommodated in the calibration wafer accommodation unit 29, the inspection is continued.

Instruction is given to start a calibration mode from the operation unit 16.

The transport robot 17 is started, and the calibration wafer 31 to match the preset inspecting condition is selected from the calibration wafer accommodation unit 29, and the calibration wafer 31 is transported to the inspection table 4.

In the calibration mode, the surface inspection of the wafer is carried out.

As the result of detection, it is judged whether the particle size output value corresponding to the particle size of the particle spread on the calibration wafer 31 has been separately detected or not. If the answer is NO, the sensitivity is adjusted on the photodetection unit, i.e. the photodetection sensor 12 or the signal processing unit 13, or on both of the photodetection sensor 12 and the signal processing unit 13. That is, the voltage applied on the photodetection sensor 12, amplification ratio of the signal processing unit 13, etc.

In case the output value of the particle size is separately detected, it is judged whether the detection level is an adequate level or not. If the answer is NO, the sensitivity of the photodetection unit is adjusted again. If it is an adequate value, the setting mode for the optimal sensitivity condition is terminated.

Next, a setting mode for low sensitivity condition is selected from the inspection menu picture, and the lowest detectable particle size is selected.

In the calibration mode, the surface inspection of the wafer is carried out.

As the result of detection, it is judged whether the particle size output value corresponding to the particle size spread on the calibration wafer 31 is within an adequate range or not. If the answer is NO, the sensitivity of the photodetection unit is adjusted. If it is judged as being within the adequate range, the setting mode for the low sensitivity condition is terminated.

Calibration measurement is performed on all particle sizes, and the setting is made between the detected particle size and the detection level.

The calibration mode is terminated. In synchronization with the termination of the calibration mode, the transport robot 17 is driven, and the calibration wafer 31 is brought back to the calibration wafer accommodation unit 29.

When the surface inspection is performed on the wafer 5 to be inspected, it is started by selecting the execution of the inspection on the inspection menu picture. Or, the sequence may be designed so that the surface inspection of the wafer 5 is carried out continuously after the completion of the calibrating operation. Or, it may be designed in such manner that a calibration sequence is incorporated in a sequence to execute the surface inspection of the wafer 5 to be inspected, and the calibrating operation and the surface inspection are continuously carried out when a command is given to execute the surface inspection from the operation unit 16.

The calibration wafer 31 is held in the wafer transport unit 1 by the calibration wafer accommodation unit 29. As a result, it is possible to continuously and automatically perform the calibration of the detection unit and the surface inspection of the wafer 5 to be inspected.

The calibration of the photodetection unit may be carried out each time the surface inspection is performed on the wafer 5 to be inspected. If the photodetection unit is stable, the calibration may be carried out periodically or at the time of maintenance inspection.

In the above embodiment, in case there are two or more calibration wafers 31, the computer 11 judges the specifications of the calibration wafers 31 depending on the inspection condition and automatically selects the wafer. It may be designed in such manner that the specifications of the calibration wafer 31 is taught to the computer. In this case, when the calibration wafer 31 is transported to the calibration wafer accommodation unit 29, the specifications of the calibration wafer 31 and the its position in the calibration wafer accommodation unit 29 are displayed on the monitor 15. Based on contents of the display, the operator may select the calibration wafer 31 and may start the calibration wafer transport program to transport the calibration wafer 31 to the inspection table 4.

Figure 8:
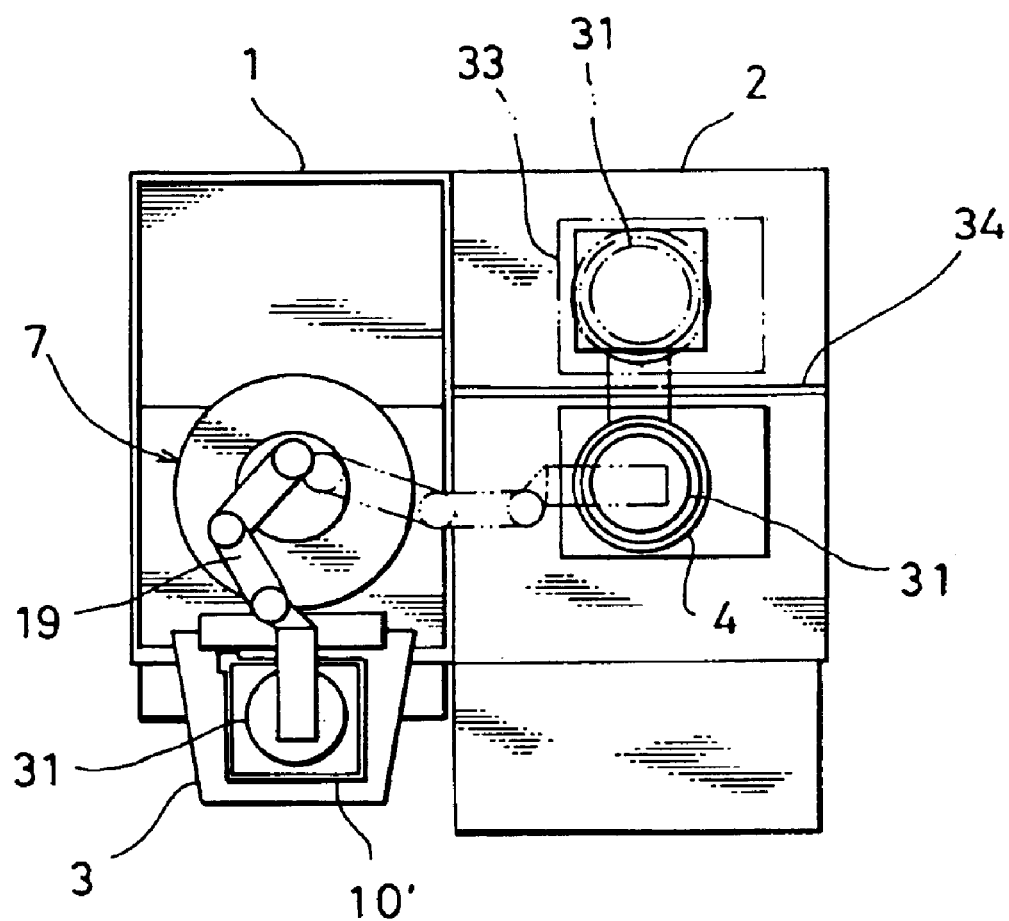
FIG. 8 is a plan view of a second embodiment of the present invention.

FIG. 8 represents a second embodiment of the present invention.

In this second embodiment, a calibration wafer accommodation unit 33 is provided in the surface inspection unit 2.

To carry out the surface inspection, the inspection table 4 is designed in such manner that it can be moved horizontally (up-to-bottom direction in FIG. 8) and can be moved up and down. In the second embodiment, the calibration wafer 31 is transported from the inspection table 4 to the calibration wafer accommodation unit 33 by utilizing the operation of the inspection table 4. Therefore, to transport the calibration wafer 31 from the cassette 10' of the cassette transfer stage 3 to the calibration wafer accommodation unit 33, the calibration wafer 31 is transported once to the inspection table 4 by the transport robot 17. Further, the calibration wafer 31 is transported to the calibration wafer accommodation unit 33 by the inspection table 4.

In case the calibration wafer 31 is accommodated in the calibration wafer accommodation unit 33, the transport of the calibration wafer 31 by the transport robot 17 as explained above in the surface inspection operation is carried out by the inspection table 4.

In FIG. 8, reference numeral 34 denotes a partition wall. For the purpose of excluding an obstacle, which hinders the transport of the calibration wafer 31 by the inspection table 4, the partition wall 34 divides the space to a space including the calibration wafer accommodation unit 33 with its lower portion opened and a space including the inspection table 4 for the surface inspection. This makes it possible to prevent the moving of particles, which may be generated due to the rotation of the inspection table 4, toward the calibration wafer accommodation unit 33 side.

As described above, the calibration wafers 31 are repeatedly used and the wafers may be kept in the surface inspection system for long time. When the wafers are stored for long time, natural or spontaneously formed oxide film may be formed on the surface of the calibration wafers 31, and this may cause changes in sensitivity to substrate noise.

In a third embodiment of the present invention, inert gas atmosphere such as nitrogen gas is used as the atmosphere in the space where the calibration wafers 31 are accommodated, and this makes it possible to prevent generation of natural oxide film.

When the open type calibration wafer accommodation unit 29 is installed in the wafer transport unit 1, clean gas delivered from the clean unit 27 is changed to nitrogen gas. In case the calibration wafer accommodation unit 29 is designed as a closed container, nitrogen gas is filled in the calibration wafer accommodation unit 29. Further, to prevent inflow of air from outside when the calibration wafer accommodation unit 29 is opened or closed, the space inside the calibration wafer accommodation unit 29 is set to positive pressure.

In case the open type calibration wafer accommodation unit 33 is provided in the surface inspection unit 2, nitrogen gas is filled in a space which includes the calibration wafer accommodation unit 33 as partitioned by the partition wall 34. When the calibration wafer accommodation unit 33 is designed as a closed container, nitrogen gas is filled under positive pressure.

When the calibration wafer accommodation unit 29 and the calibration wafer accommodation unit 33 are designed as closed containers and inert gas is filled under positive pressure, a pressure regulating valve (not shown) may be arranged on a gas supply and discharge line (not shown) to the calibration wafer accommodation unit 29 and the calibration wafer accommodation unit 33. By controlling pressure, it is possible that no substantial gas flow does not occur due to the pressure difference between inside and outside of the closed container when the calibration wafer accommodation unit 29 and the calibration wafer accommodation unit 33 are opened or closed.

According to the present invention, the surface inspection system comprises a calibration wafer where particles of known specifications are spread, a wafer transport unit having a transport robot, a surface inspection unit and a calibration wafer accommodation unit for accommodating the calibration wafer. This makes it possible to eliminate procedure to bring the calibration wafer in and out of the surface inspection system, and this contributes to the improvement of working efficiency.

The calibration wafer accommodation unit is designed as an airtight dustproof space, which can be opened or closed, and this makes it possible to prevent the attachment of the particles to the calibration wafer to be accommodated.

Because the calibration wafer accommodation unit holds and accommodates the calibration wafers in a vertical position, the attachment of the particles can be prevented.

The calibration wafer accommodation unit is arranged at a position above a wafer receiving plane of the surface inspection unit. This prevents the attachment of the particles, which may be generated during surface inspection.

A clean unit is provided in the wafer transport unit, and the clean unit delivers clean air into the wafer transport unit. The calibration wafer accommodation unit is positioned upstream of a flow of the clean air with respect to the transport robot, and this prevents the attachment of the particles to the calibration wafers.

The surface inspection unit comprises a computer which has a surface inspection program, a calibration program, and a transport robot driving program. The transport robot driving program, the surface inspection program, and the calibration program are executed, and bringing of the calibration wafer into the surface inspection unit by the transport robot, surface inspection of the calibration wafer, execution of calibration, and bringing out of the calibration wafer are sequentially carried out. Thus, the calibrating operation can be automatically performed, and this leads to further improvement of working efficiency.

An inert gas atmosphere is used as the atmosphere around the calibration wafer. This prevents formation of natural or spontaneously formed oxide film and eliminates the change of surface conditions. Also, this makes it possible to perform the surface inspection in stable manner for long time.

What is claimed is:

1. A surface inspection system, comprising a wafer transport unit having a wafer transport space and a transport robot accommodated in said wafer transport space, a surface inspection unit having a a wafer receiving plane in which said wafer is received, a calibration wafer accommodation unit for accommodating a calibration wafer where particles of known specifications are spread, a clean unit which delivers clean air, and a flow of the clean air which is delivered from said clean air unit and which flows from said calibration wafer accommodation unit to said wafer transport space, wherein said calibration wafer accommodation unit is arranged in the flow of clean air and is arranged at a position above said wafer receiving plane of said surface inspection unit and said calibration wafer accommodation unit is positioned within said flow of clean air, upstream of said wafer receiving plane.

2. A surface inspection system according to claim 1, wherein said calibration wafer accommodation unit has an airtight dustproof container which can be opened and closed, wherein said container accommodates said calibration wafer.

3. A surface inspection system according to claim 1, wherein said calibration wafer accommodation unit is provided in said wafer transport unit.

4. A surface inspection unit according to claim 1, wherein a wafer to be inspected which is inspected in said wafer inspection unit is transported between said wafer transport unit and said wafer receiving plane, and said calibration wafer is transported between said wafer receiving plane and said calibration wafer accommodation unit.

5. A surface inspection system according to claim 1, wherein said calibration wafer accommodation unit holds and accommodates said calibration wafer in a vertical position.

6. A surface inspection system according to claim 1, wherein said surface inspection unit comprises a computer, and said calibration wafer accommodation unit accommodates one or more additional calibration wafers and said computer records a transport history of each of said calibration wafers.

7. A surface inspection system according to claim 1, wherein said wafer inspection unit is provided adjacent to said wafer transport unit; said wafer transport unit has said wafer accommodation unit for accommodating said calibration wafer in an upper portion of said wafer transport unit, and said wafer transport unit has said wafer transport space in a middle portion of said wafer transport unit; and said transport robot is moved up and down between said wafer transport space and said calibration wafer accommodation unit so as to transport said calibration wafer, and said transport robot is moved horizontally between said wafer transport space and said surface inspection unit so as to transport said calibration wafer.

8. A surface inspection system according to claim 1, wherein said surface inspection unit comprises a computer, which has a wafer surface inspection program, a calibration program, and a transport robot driving program, wherein said transport robot driving program, said surface inspection program, and said calibration program are executed, and transporting said calibration wafer into said surface inspection unit by said transport robot, surface inspection of said calibration wafer, execution of calibration, and removing said calibration wafer are sequentially carried out.

9. A surface inspection system according to claim 2, wherein an inert gas is filled in said calibration wafer accommodation unit.

* * * * *